(12) United States Patent
Lv et al.

(10) Patent No.: US 11,132,799 B2
(45) Date of Patent: Sep. 28, 2021

(54) METHOD AND SYSTEM FOR CLASSIFYING DIABETIC RETINA IMAGES BASED ON DEEP LEARNING

(71) Applicant: BOZHON PRECISION INDUSTRY TECHNOLOGY CO., LTD., Suzhou (CN)

(72) Inventors: Shaolin Lv, Suzhou (CN); Jiangbing Zhu, Suzhou (CN); Qian Wang, Suzhou (CN); Ruixia Chen, Suzhou (CN)

(73) Assignee: BOZHON PRECISION INDUSTRY TECHNOLOGY CO., LTD., Suzhou (CN)

(*) Notice: Subject to any disclaimer, the term of this patent is extended or adjusted under 35 U.S.C. 154(b) by 24 days.

(21) Appl. No.: 16/835,199

(22) Filed: Mar. 30, 2020

(65) Prior Publication Data
US 2020/0234445 A1 Jul. 23, 2020

Related U.S. Application Data

(63) Continuation of application No. PCT/CN2048/098390, filed on Aug. 2, 2018.

(30) Foreign Application Priority Data

Aug. 2, 2018 (CN) .......................... 201810330385.6

(51) Int. Cl.
*G06T 7/00* (2017.01)
*G16H 30/40* (2018.01)
(Continued)

(52) U.S. Cl.
CPC .......... *G06T 7/0014* (2013.01); *G06N 20/10* (2019.01); *G06T 5/002* (2013.01); *G06T 5/20* (2013.01);
(Continued)

(58) Field of Classification Search
None
See application file for complete search history.

(56) References Cited

U.S. PATENT DOCUMENTS 8,879,813 B1 * 11/2014 Solanki .................... A61B 3/14
382/128
9,795,301 B2 * 10/2017 Fleming ............... A61B 5/0066
(Continued)

FOREIGN PATENT DOCUMENTS

CN     103870838 A     6/2014
CN     107203778 A     9/2017
(Continued)

OTHER PUBLICATIONS

Ronneberger et al., "U-Net Convolutional Networks for Biomedical Image Segmentation", Medical Image Computer-Assisted Intervention-MICCAI, 2015, pp. 234-241.

*Primary Examiner* — Jiangeng Sun
(74) *Attorney, Agent, or Firm* — SZDC Law PC

(57) ABSTRACT

A method for classifying diabetic retina images based on deep learning includes: obtaining a fundus image; importing the same fundus image into a microhemangioma lesion recognition model, a hemorrhage lesion recognition model and an exudation lesion recognition model for recognition; extracting lesion feature information from the recognition results, and then using a trained support vector machine classifier to classify the extracted lesion feature information to obtain a classification result. The microhemangioma lesion recognition model is obtained by extracting a candidate microhemangioma lesion region in the fundus image and inputting it into a CNN model for training; the hemorrhage lesion recognition model and the exudation lesion recognition model are obtained by labeling a region in the fundus image as a hemorrhage lesion region and an exuda- (Continued)

tion lesion region, and then inputting the result into an FCN model for training. A system for the same is also disclosed.

10 Claims, 3 Drawing Sheets

(51) Int. Cl.
    *G06N 20/10*      (2019.01)
    *G06T 5/00*      (2006.01)
    *G06T 5/20*      (2006.01)

(52) U.S. Cl.
    CPC ... *G16H 30/40* (2018.01); *G06T 2207/20081* (2013.01); *G06T 2207/20084* (2013.01); *G06T 2207/20182* (2013.01); *G06T 2207/30041* (2013.01); *G06T 2207/30096* (2013.01)

(56) References Cited

U.S. PATENT DOCUMENTS

| | | | |
|---|---|---|---|
| 2018/0315193 A1* | 11/2018 | Paschalakis | G06N 3/08 |
| 2019/0206054 A1* | 7/2019 | Mao | A61B 3/12 |

FOREIGN PATENT DOCUMENTS

| | | | | |
|---|---|---|---|---|
| CN | 107330449 A | 11/2017 | | |
| CN | 107423571 A | 12/2017 | | |
| CN | 107680684 A | 2/2018 | | |
| WO | 2016132115 A1 | 8/2016 | | |
| WO | WO-2017031099 A1 * | 2/2017 | | G06T 7/0012 |
| WO | WO-2019231102 A1 * | 12/2019 | | G16H 30/20 |

\* cited by examiner

METHOD AND SYSTEM FOR CLASSIFYING DIABETIC RETINA IMAGES BASED ON DEEP LEARNING

This application is the continuation application of PCT/CN2018/098390, filed Aug. 2, 2018, which claims the priority benefit of Chinese Patent Application No. 201810330385.6 filed on Apr. 13, 2018, and entitled "Method and system for classifying diabetic retina images based on deep learning" which is incorporated by reference in its entirety.

TECHNICAL FIELD

The present invention relates to the field of artificial intelligence, and discloses a method and system for classifying diabetic retina images based on deep learning.

BACKGROUND

The number of diabetics in China is huge and showing a rising trend year by year. Diabetic retinopathy is one of the serious complications of diabetes, and also the main cause of blindness in people 20 to 65 years old. It not only causes great harm and burden to the society and the families of diabetics, but also greatly reduces the quality of life of diabetics.

Because blindness caused by diabetic retinopathy is preventable, early detection and early intervention are the most effective means to prevent blindness caused by diabetes. However, in the early stages of retinopathy caused by diabetes, patients basically have no discomfort, so retinopathy is easy to be ignored without screening, which delays treatment and causes irreversible damage to vision.

At present, deep learning is widely used in medical image processing, which can greatly improve the efficiency of clinical screening. Currently, mature deep learning models all use a supervised learning model. However, a large amount of high-quality labeled medical image data is difficult to obtain, resulting in medical images used in deep learning training generally lagging behind natural images; especially in diabetic retinopathy, the patients' retinal fundus images are complicated and a variety of lesions coexist, so it is difficult to improve the detection efficiency with limited materials. Therefore, how to use a small training set to obtain a model with strong generalization ability is an urgent problem to be solved in the application of deep learning in the medical field.

SUMMARY

In view of the above shortcomings in the prior art, the present invention proposes a method and system for classifying diabetic retina images based on deep learning, which reduces the requirement for the description ability of the network model so as to make the model easy to train, and can locate and outline the lesion regions for different lesions so as to facilitate clinical screening.

The present invention is implemented by the following technical solution:

The present invention relates to a method for classifying diabetic retina images based on deep learning, which comprises the following steps:

obtaining a fundus image to be recognized; and importing the same fundus image to be recognized respectively into a microhemangioma lesion recognition model, a hemorrhage lesion recognition model and an exudation lesion recognition model for recognition; extracting lesion feature information from the recognition results, and then using a trained support vector machine (SVM) classifier to classify the extracted lesion feature information to obtain a lesion grade classification result corresponding to the fundus image.

The microhemangioma lesion recognition model is obtained by extracting a candidate microhemangioma lesion region in the fundus image, labeling the region as a microhemangioma or non-microhemangioma lesion region, and then inputting the result into a CNN model for training;

the hemorrhage lesion recognition model is obtained by labeling a region in the fundus image as a hemorrhage or non-hemorrhage lesion region, and then inputting the result into an FCN model for training; and the exudation lesion recognition model is obtained by labeling a region in the fundus image as an exudation lesion region or a non-exudation lesion region, and then inputting the result into the FCN model for training.

The microhemangioma lesion recognition model is obtained based on CNN model training through the following steps:

A1. image preprocessing: extracting a green channel image, using r-polynomial transformation to correct grayscale of the green channel image, and then using Gaussian filtering to denoise the image to obtain a corrected image $I'_W$;

A2. extraction of the candidate microhemangioma lesion region $I_{candidate}$: randomly selecting a pixel point in the corrected image $I'_W$, and using this pixel point as a reference and an angle $\alpha$ as a step size to generate linear structural elements of different scales; using the generated linear structural elements to perform morphological processing on the corrected image $I'_W$, to obtain response results of the linear structural elements of different scales; keeping the minimum response result $I_{closed}$ corresponding to each pixel point to get $I_{candidate} = I_{closed} - I'_W$, and then performing hybrid threshold segmentation-extraction on $I_{candidate}$;

A3. data labeling: labeling segmentation-extraction results of the candidate microhemangioma lesion region $I_{candidate}$ as lesion and non-lesion to generate a training set; and A4. model training: inputting the training set into the CNN model for training, to obtain the microhemangioma lesion recognition model.

Both the hemorrhage lesion recognition model and the exudation lesion recognition model are obtained based on FCN model training through the following steps:

B1. labeling a region in the fundus image as a lesion or non-lesion region by image processing to generate a training set; and B2. using a U-net network structure to build the FCN model, and each time randomly taking a part of the labeled data in the training set for training, to obtain a trained lesion recognition model, wherein DICE is used as a cost function for the training.

The labeling a region in the fundus image also generates a test set, which is used to test the trained model to evaluate the recognition ability of the trained model.

The labeling a region in the fundus image also generates a validation set, which is used for correction in the model training to prevent network overfitting.

The image processing comprises the following steps:

C1. extracting a fundus region from the image;

C2. using median filtering to perform image enhancement on the extracted fundus region, and then performing grayscale normalization on the enhanced result; and C3. performing threshold segmentation on the normalization result, and then using an area feature to screen out the candidate lesion region.

The SVM classifier is obtained by classifying and training the lesion feature information corresponding to the training set.

The lesion feature information includes, but is not limited to, the number, area, shape, grayscale, roundness, and aspect ratio of the lesion region.

A system for classifying diabetic retina images based on the above method, comprising:

a microhemangioma recognition module, used to recognize a to-be-examined image by using the microhemangioma lesion recognition model, and label a microhemangioma lesion location in the to-be-examined image, so as to obtain corresponding lesion characteristic parameters;

a hemorrhage recognition module, used to recognize a to-be-examined image by using the hemorrhage lesion recognition model, and segment a recognized hemorrhage lesion region, so as to obtain corresponding lesion characteristic parameters;

an exudation recognition module, used to recognize a to-be-examined image by using the exudation lesion recognition model, and segment a recognized exudation lesion region, so as to obtain corresponding lesion characteristic parameters;

a classification module, used to classify the characteristic parameters of each lesion region obtained by recognizing the to-be-examined image, so as to obtain lesion grade classification results of the to-be-examined image.

Technical Effects

The present invention respectively recognizes microhemangioma, hemorrhage, and exudation lesions based on deep learning, and can automatically label the position and size of the lesion regions. Compared with the traditional method of artificially extracting features in combination with image processing, the present invention reduces the difficulty in developing the diabetic retinopathy recognition system. Because the present invention adopts different neural network models for different lesions, the saved model has higher accuracy and stronger applicability for specific lesion recognition. The present invention, integrating multiple features of three lesions including microhemangioma, hemorrhage and exudation for classification, has higher classification accuracy, and can more effectively assist doctors in clinical screening.

DETAILED DESCRIPTION OF PREFERRED EMBODIMENTS

The present invention will be described below in detail with reference to drawings and embodiments.

Example 1

Figure 1:
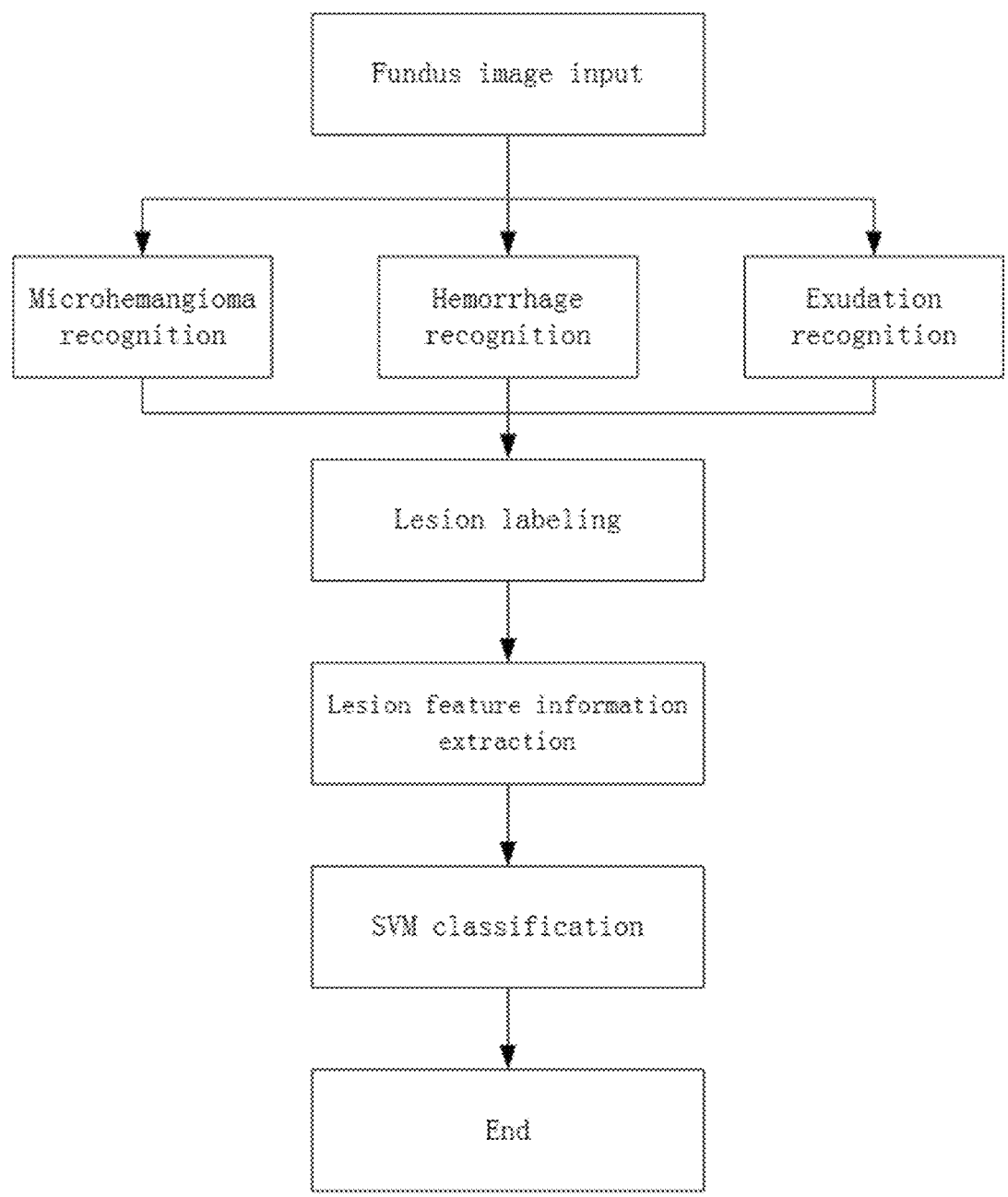
FIG. 1 is a flowchart of a method in Example 1.

As shown in FIG. 1, Example 1 related to a method for classifying diabetic retina images based on deep learning, which comprised the following steps:

obtaining a fundus image to be recognized; and importing the same fundus image to be recognized respectively into a microhemangioma lesion recognition model, a hemorrhage lesion recognition model and an exudation lesion recognition model for recognition; extracting lesion feature information from the recognition results, and then using a trained SVM classifier to classify the extracted lesion feature information to obtain a lesion grade classification result corresponding to the fundus image.

The microhemangioma lesion recognition model was obtained by extracting a candidate microhemangioma lesion region in the fundus image, labeling the region as a microhemangioma or non-microhemangioma lesion region, and then inputting the result into a CNN model for training;

the hemorrhage lesion recognition model was obtained by labeling a region in the fundus image as a hemorrhage or non-hemorrhage lesion region, and then inputting the result into an FCN model for training; and the exudation lesion recognition model was obtained by labeling a region in the fundus image as an exudation lesion region or a non-exudation lesion region, and then inputting the result into the FCN model for training.

Figure 2:
FIG. 2 is an extraction effect diagram of a candidate microhemangioma region in Example 1.

The microhemangioma lesion recognition model was obtained based on CNN model training through the following steps:

A1. image preprocessing: extracting a green channel image, using r-polynomial transformation to correct grayscale of the green channel image, and then using Gaussian filtering to denoise the image to obtain a corrected image $I'_W$; the r-polynomial transformation was as follows:

$$I_w(i,j) = f(x) = \begin{cases} \dfrac{\frac{1}{2}(\mu_{max} - \mu_{min})}{(\mu_W(i,j) - \min(G))^r}, & G(i,j) \le \mu_w(i,j) \\ \dfrac{-\frac{1}{2}(\mu_{max} - \mu_{min})}{(\mu_W(i,j) - \max(G))^r}, & G(i,j) > \mu_w(i,j) \end{cases}$$

where r was a power of a polynomial and had a value of 2, $\mu_{min}$ was the minimum grayscale value, and had a value of 0, $\mu_{max}$ was the maximum grayscale value, and had a value of 1, G was the extracted green channel image, $\mu_W(i,j)$ was the average grayscale value in a neighborhood of the green channel image with (i, j) as the center and W as the radius, and $I_W$ was a grayscale equalized image obtained through the r-polynomial transformation;

A2. extraction of the candidate microhemangioma lesion region $I_{candidate}$: randomly selecting a pixel point in the corrected image $I'_W$, and using this pixel point as a reference and an angle of 10° to 25°, preferably 15°, as a step size to generate linear structural elements of different scales; using the generated linear structural elements to perform morphological processing on the corrected image $I'_W$, to obtain response results of the linear structural elements of different scales; keeping the minimum response result $I_{closed}$ corresponding to each pixel point to get $I_{candidate} = I_{closed} - I'_W$, and then performing hybrid threshold segmentation-extraction on $I_{candidate}$ with the extraction effect shown in FIG. 2;

the hybrid threshold segmentation-extraction was based on the following conditions:

$$t_K = \begin{cases} t_l, & \forall t_s: CC(I_{candidate} > t_s) < K \\ t_k, & CC(I_{candidate} > t_s) \leq K \\ t_u, & \forall t_s: CC(I_{candidate} > t_s) > K \end{cases}$$

where K was a constant representing the maximum number (preferably 120) of the candidate microhemangioma lesion regions in the morphological processing, and CC represented a function of counting the number of the candidate lesion regions;

$t_l$ was the minimum threshold, $t_u$ was the maximum threshold, $t_k$ was a threshold meeting CC conditions, and $t_s$ was a threshold gradually increasing in a step size of 0.002; increasing $t_s$ from the minimum value of $I_{candidate}$ to the maximum grayscale value of $I_{candidate}$ according to the minimum grayscale interval until the number counted by the function CC met the conditions of the above formulas, and then using the threshold $t_K$ to binarize $I_{candidate}$ to extract a binary map of the candidate microhemangioma lesion region;

A3. data labeling: labeling segmentation-extraction results of the candidate microhemangioma lesion region $I_{candidate}$ as lesion and non-lesion to generate a training set; and A4. model training: inputting the training set into the CNN model for training, to obtain the microhemangioma lesion recognition model.

Figure 3:
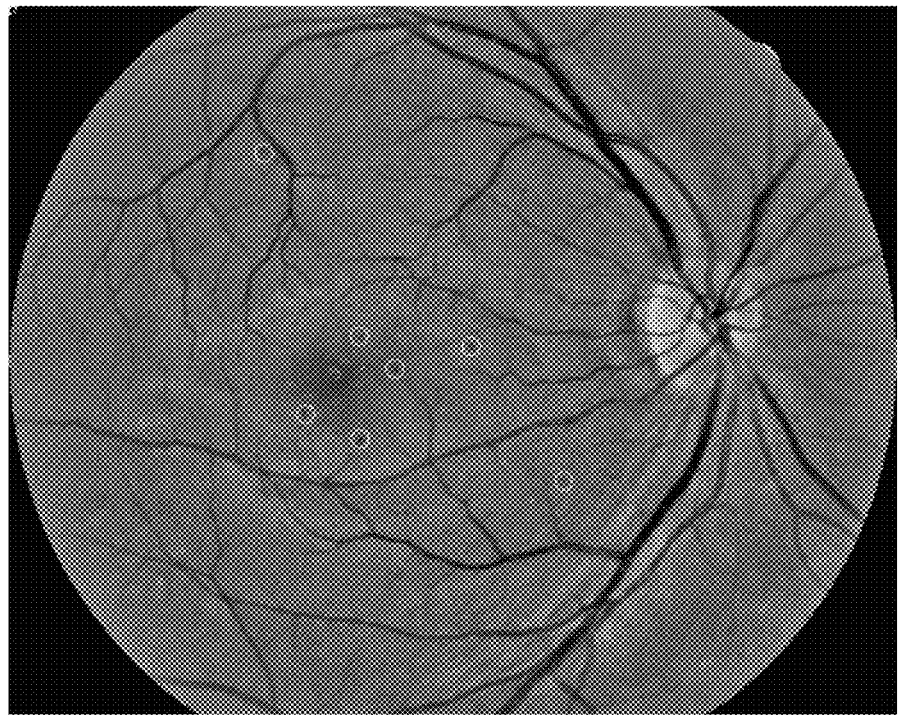
FIG. 3 is a labeled diagram of a microhemangioma lesion region in Example 1.

Here, we used 400 fundus images containing microhemangioma for training. The sensitivity and specificity of the model obtained after training on whether the segmentation site was classified as microhemangioma reached 90%. The microhemangioma lesion region finally obtained was shown in FIG. 3.

Both the hemorrhage lesion recognition model and the exudation lesion recognition model were obtained based on FCN model training through the following steps:

B1. labeling a region in the fundus image as a lesion or non-lesion region by image processing to generate a training set; and B2. using a U-net network structure to build the FCN model, and each time randomly taking a part of the labeled data in the training set for training, to obtain a trained lesion recognition model, wherein DICE was used as a cost function for the training.

The cost function DICE was as follows:

$$s = \frac{2|X \cap Y|}{|X| + |Y|},$$

where X was a label graph, and Y was a result graph.

The labeling a region in the fundus image also generated a test set, which was used to test the trained model to evaluate the recognition ability of the trained model.

The labeling a region in the fundus image also generated a validation set, which was used for correction in the model training so as to adjust the network parameters and prevent network overfitting; the validation set could also be used to determine the network structure and control the model complexity; depending on the different validation set, there were differences in the results obtained after the input of the test set; according to the situation, we could choose the optimal model that met our needs.

The image processing algorithm comprised the following specific steps:

C1. extracting a fundus region from the image;

C2. using median filtering to perform image enhancement on the extracted fundus region, and then performing grayscale normalization on the enhanced result; and C3. performing threshold segmentation on the normalization result, and then using an area feature to perform region screening to obtain the segmentation result.

Using the FCN model for hemorrhage and exudation recognition could also adjust the proportion of lesion samples, pass-examination samples and miss-examination samples in the training samples according to the actual data distribution, so as to improve the accuracy and generalization ability of the model without redesigning the algorithm, thereby reducing the intensity of algorithm development and improving the efficiency of algorithm development.

Figure 4:
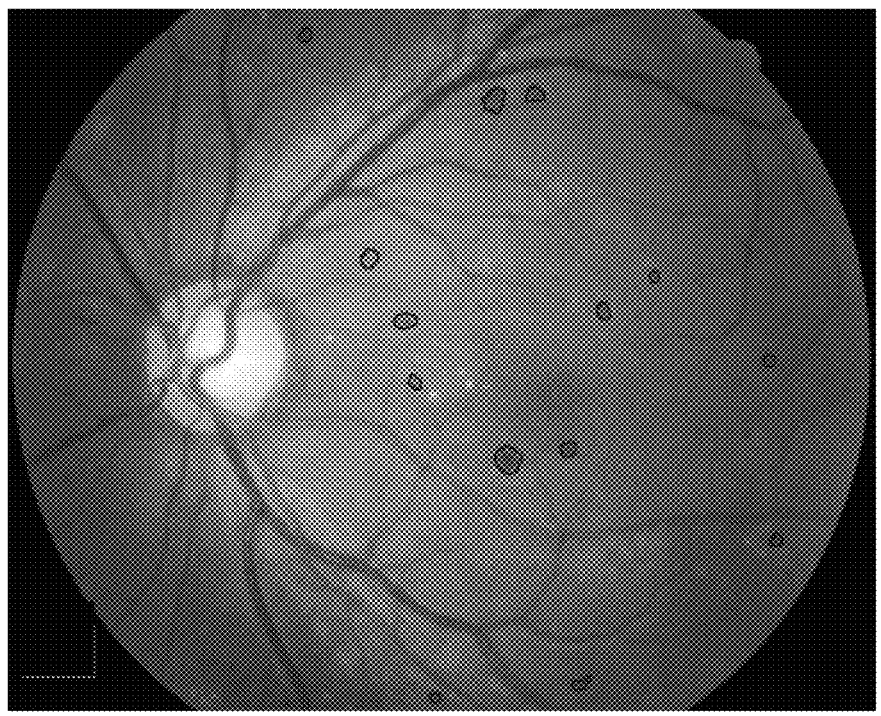
FIG. 4 is a labeled diagram of a hemorrhage lesion location in Example 1.

Because the area of the hemorrhage lesion region was generally large, it was suitable to use the trained hemorrhage lesion recognition model to segment the hemorrhage region in the image. We could use the image processing algorithm to obtain the corresponding lesion region and non-lesion region segmentation results and get the hemorrhage lesion recognition model; in the training, we labeled a total of 1,000 training samples with hemorrhage. In order to suppress pass-examination, 400 training samples without hemorrhage were added for training. After testing, the specificity of the model for recognizing fundus hemorrhage reached 89%, the sensitivity for recognizing hemorrhage in DR2 data reached 89%, and the sensitivity for recognizing hemorrhage in DR3 data was 100%. The effect of recognizing hemorrhage was shown in FIG. 4.

Figure 5:
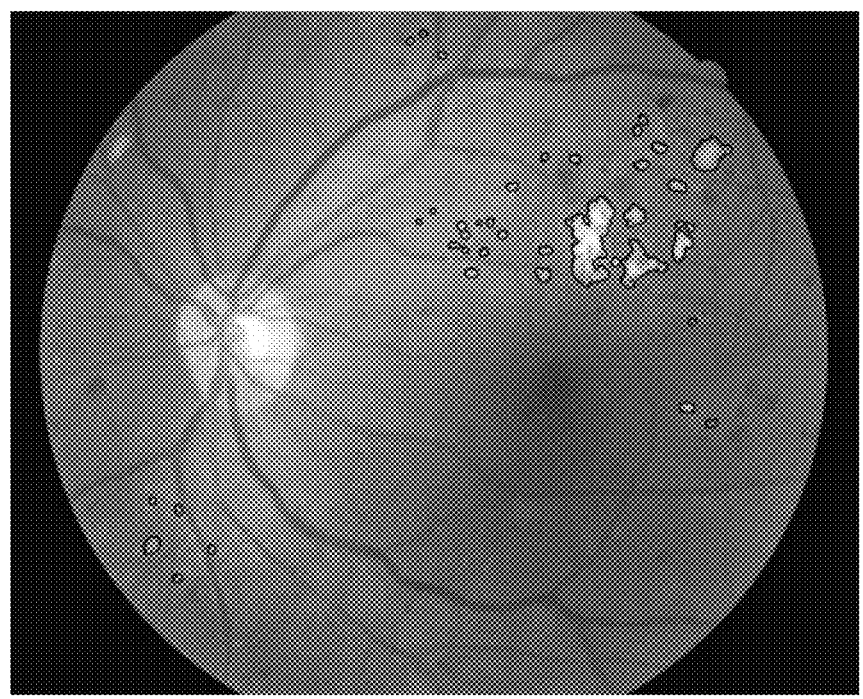
FIG. 5 is a labeled diagram of an exudation lesion location in Example 1.

Since exudation was obviously different in morphology and color from other normal fundus structures, exudation recognition was less difficult than hemorrhage recognition, so using the exudation lesion recognition model could obtain good recognition results. We could use the image processing algorithm to obtain the corresponding lesion region and non-lesion region segmentation results and get the exudation lesion recognition model. In the training, we labeled a total of 800 training samples with exudation. In order to suppress pass-examination, 300 training samples without exudation and 100 samples with lesions similar to exudation (a nerve fiber layer, drusen) were added for training. The resulting model had a sensitivity of 86% and a specificity of 87% for judging whether the image had exudation. The effect of recognizing exudation was shown in FIG. 5.

Since the recognition result of each lesion could not be 100% accurate, staging directly according to the clinical staging criteria based on the recognition result of each lesion would result in a lower specificity of the image diagnosis result. Therefore, we used the recognition results of the three lesions as features to train the SVM classifier to judge the final diagnosis result of the image, finding that the sensitivity of DR3 recognition was more than 99%, the sensitivity of DR2 recognition reached 85%, the sensitivity of DR1 recognition reached 80%, and the specificity was 80%.

Through the above method, we not only got a high accuracy in identifying the presence or absence of lesions in the image, but also labeled the location of the lesion region in the image.

The lesion feature information extracted from the recognition results of the microhemangioma lesion recognition model, the hemorrhage lesion recognition model and the exudation lesion recognition model was combined and inputted into the SVM classifier for training, thus obtaining the trained SVM classifier.

The lesion feature information included, but is not limited to, the number, area, shape, grayscale, roundness, and aspect ratio of the lesion region.

A system for classifying diabetic retina images based on the above method was provided, comprising:

a microhemangioma recognition module, used to recognize a to-be-examined image by using the microhemangioma lesion recognition model, and label a microhemangioma lesion location in the to-be-examined image, so as to obtain corresponding lesion characteristic parameters;

a hemorrhage recognition module, used to recognize a to-be-examined image by using the hemorrhage lesion recognition model, and segment a recognized hemorrhage lesion region, so as to obtain corresponding lesion characteristic parameters;

an exudation recognition module, used to recognize a to-be-examined image by using the exudation lesion recognition model, and segment a recognized exudation lesion region, so as to obtain corresponding lesion characteristic parameters; and a classification module, used to classify the characteristic parameters of each lesion region obtained by recognizing the to-be-examined image, so as to obtain lesion grade classification results of the to-be-examined image.

The example of the present invention is scalable and currently includes models for recognizing three typical diabetic fundus lesions. With the pathological changes of the disease and the need for detection, we can train the recognition model of the corresponding lesion with the deep learning technology, and increase the recognition module of the corresponding lesion.

It should be emphasized that the above example is only a preferred example of the present invention, and does not limit the present invention in any form; any simple amendments, equivalent changes, and modifications made to the above example in accordance with the technical essence of the present invention still fall within the scope of the technical solution of the present invention.

What is claimed is:

1. A method for classifying diabetic retina images based on deep learning, which is characterized in that the method comprises the following steps:

obtaining a fundus image to be recognized;

importing the same fundus image to be recognized respectively into a microhemangioma lesion recognition model, a hemorrhage lesion recognition model and an exudation lesion recognition model for recognition; extracting lesion feature information from recognition results, and then using a trained support vector machine (SVM) classifier to classify the extracted lesion feature information to obtain a lesion grade classification result corresponding to the fundus image;

the microhemangioma lesion recognition model is obtained by extracting a candidate microhemangioma lesion region in the fundus image, labeling the region as a microhemangioma or non-microhemangioma lesion region, and then inputting the result into a CNN model for training;

the hemorrhage lesion recognition model is obtained by labeling a region in the fundus image as a hemorrhage or non-hemorrhage lesion region, and then inputting the result into an FCN model for training; and the exudation lesion recognition model is obtained by labeling a region in the fundus image as an exudation lesion region or a non-exudation lesion region, and then inputting the result into the FCN model for training.

2. The method for classifying diabetic retina images based on deep learning according to claim 1, characterized in that: the microhemangioma lesion recognition model is obtained based on CNN model training through the following steps:

A1, image preprocessing: extracting a green channel image, using r-polynomial transformation to correct grayscale of the green channel image, and then using Gaussian filtering to denoise the image to obtain a corrected image $I'_W$;

A2, extraction of the candidate microhemangioma lesion region $I_{candidate}$: randomly selecting a pixel point in the corrected image $I'_W$, and using this pixel point as a reference and an angle α as a step size to generate linear structural elements of different scales; using the generated linear structural elements to perform morphological processing on the corrected image $I'_W$, to obtain response results of the linear structural elements of different scales; keeping the minimum response result $I_{closed}$ corresponding to each pixel point to get $I_{candidate} = I_{closed} - I'_W$, and then performing hybrid threshold segmentation-extraction on $I_{candidate}$;

A3, data labeling: labeling segmentation-extraction results of the candidate microhemangioma lesion region $I_{candidate}$ as lesion or non-lesion to generate a training set; and A4, model training: inputting the training set into the CNN model for training, to obtain the microhemangioma lesion recognition model.

3. The method for classifying diabetic retina images based on deep learning according to claim 2, characterized in that: the r-polynomial transformation is as follows:

$$I_w(i,j) = f(x) = \begin{cases} \dfrac{\frac{1}{2}(\mu_{max} - \mu_{min})}{(\mu_W(i,j) - \min(G))^r}, & G(i,j) \le \mu_w(i,j) \\ -\dfrac{\frac{1}{2}(\mu_{max} - \mu_{min})}{(\mu_W(i,j) - \max(G))^r}, & G(i,j) > \mu_w(i,j) \end{cases}$$

where r is a power of a polynomial and has a value of 2, $\mu_{min}$ is the minimum grayscale value, and has a value of 0, $\mu_{max}$ is the maximum grayscale value, and has a value of 1, G is the extracted green channel image, $\mu_W(i,j)$ is the average grayscale value in a neighborhood of the green channel image with (i, j) as the center and W as the radius, and $I_W$ is a grayscale equalized image obtained through the r-polynomial transformation.

4. The method for classifying diabetic retina images based on deep learning according to claim 2, characterized in that: the hybrid threshold segmentation-extraction is based on the following conditions:

$$t_K = \begin{cases} t_l, & \forall t_s: CC(I_{candidate} > t_s) < K \\ t_k, & CC(I_{candidate} > t_s) \le K \\ t_u, & \forall t_s: CC(I_{candidate} > t_s) > K \end{cases}$$

where K is a constant representing the maximum number of the candidate microhemangioma lesion regions in the morphological processing, and CC represents a function of counting the number of the candidate lesion regions;

$t_l$ is the minimum threshold, $t_u$ is the maximum threshold, $t_k$ is a threshold meeting CC conditions, and $t_s$ is a threshold gradually increasing in a step size of 0.001-0.004;

increasing $t_s$ from the minimum value of $I_{candidate}$ to the maximum grayscale value of $I_{candidate}$ according to the minimum grayscale interval until the number counted by the function CC meets the conditions of the above formulas, and then using the threshold $t_k$ to binarize $I_{candidate}$ to extract a binary map of the candidate microhemangioma lesion region.

5. The method for classifying diabetic retina images based on deep learning according to claim 1, characterized in that: both the hemorrhage lesion recognition model and the exudation lesion recognition model are obtained based on FCN model training through the following steps:
   B1, labeling a region in the fundus image as a lesion or non-lesion region by image processing to generate a training set; and
   B2, using a U-net network structure to build the FCN model, and each time randomly taking a part of the labeled data in the training set for training, to obtain a trained lesion recognition model, wherein DICE is used as a cost function for the training.

6. The method for classifying diabetic retina images based on deep learning according to claim 1, characterized in that: the labeling a region in the fundus image also generates a test set, which is used to test the trained model to evaluate the recognition ability of the trained model.

7. The method for classifying diabetic retina images based on deep learning according to claim 1, characterized in that: the labeling a region in the fundus image also generates a validation set, which is used for correction in the model training to prevent network overfitting.

8. The method for classifying diabetic retina images based on deep learning according to claim 1, characterized in that: the SVM classifier is obtained by classifying and training the lesion feature information corresponding to the training set.

9. The method for classifying diabetic retina images based on deep learning according to claim 8, characterized in that: the lesion feature information includes the number, area, shape, grayscale, roundness, and aspect ratio of the lesion region.

10. A system for classifying diabetic retina images based on the method according to any of the above claims, comprising:
   a microhemangioma recognition module, used to recognize a to-be-examined image by using the microhemangioma lesion recognition model, and label a microhemangioma lesion location in the to-be-examined image, so as to obtain corresponding lesion characteristic parameters;
   a hemorrhage recognition module, used to recognize a to-be-examined image by using the hemorrhage lesion recognition model, and segment a recognized hemorrhage lesion region, so as to obtain corresponding lesion characteristic parameters;
   an exudation recognition module, used to recognize a to-be-examined image by using the exudation lesion recognition model, and segment a recognized exudation lesion region, so as to obtain corresponding lesion characteristic parameters; and
   a classification module, used to classify the characteristic parameters of each lesion region obtained by recognizing the to-be-examined image, so as to obtain lesion grade classification results of the to-be-examined image.

* * * * *